(12) United States Patent
Inoue et al.

(10) Patent No.: US 12,247,330 B2
(45) Date of Patent: Mar. 11, 2025

(54) CYLINDRICAL STRUCTURE

(71) Applicant: Murata Manufacturing Co., Ltd., Nagaokakyo (JP)

(72) Inventors: Takafumi Inoue, Nagaokakyo (JP); Masayuki Tsuji, Nagaokakyo (JP); Eiji Taguchi, Nagaokakyo (JP); Hirokazu Hayashi, Osaka (JP); Ryosuke Ebina, Osaka (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 371 days.

(21) Appl. No.: 17/716,032

(22) Filed: Apr. 8, 2022

(65) Prior Publication Data
US 2022/0228300 A1   Jul. 21, 2022

Related U.S. Application Data

(63) Continuation of application No. PCT/JP2020/043597, filed on Nov. 24, 2020.

(30) Foreign Application Priority Data

Nov. 25, 2019   (JP) .................. 2019-212117

(51) Int. Cl.
  *D03D 3/02*   (2006.01)
  *A61L 9/16*   (2006.01)
  (Continued)

(52) U.S. Cl.
  CPC .................. *D03D 3/02* (2013.01); *A61L 9/16* (2013.01); *D03D 15/533* (2021.01); *D04B 1/16* (2013.01);
  (Continued)

(58) Field of Classification Search
  CPC .......... D03D 3/02; D04B 1/16; H10N 30/702; A61L 2209/132
  See application file for complete search history.

(56) References Cited

U.S. PATENT DOCUMENTS

| 5,410,210 A * | 4/1995 | Sato ...................... H10N 30/87 |
| | | 310/800 |
| 2018/0108826 A1* | 4/2018 | Tajitsu ................... H10N 30/87 |

(Continued)

FOREIGN PATENT DOCUMENTS

| CN | 110088366 A | 8/2019 |
| JP | 2009185397 A | 8/2009 |

(Continued)

OTHER PUBLICATIONS

International Search Report issued for PCT/JP2020/043597, date of mailing Jan. 26, 2021.

(Continued)

*Primary Examiner* — Michael Zhang
(74) *Attorney, Agent, or Firm* — ArentFox Schiff LLP

(57) ABSTRACT

A cylindrical structure including a first cloth including a piezoelectric thread that generates an electric potential from external energy, a second cloth including a piezoelectric thread that generates an electric potential from external energy, and a connection portion connecting the first cloth and the second cloth, wherein the first cloth and the second cloth forms a side face of the cylindrical structure.

13 Claims, 7 Drawing Sheets

(51) Int. Cl.
  *D03D 15/533* (2021.01)
  *D04B 1/16* (2006.01)
  *H10N 30/00* (2023.01)
  *H10N 30/857* (2023.01)

(52) U.S. Cl.
  CPC ......... *H10N 30/702* (2024.05); *H10N 30/857* (2023.02); *A61L 2209/132* (2013.01); *D10B 2401/16* (2013.01)

(56) References Cited

U.S. PATENT DOCUMENTS

| | | |
|---|---|---|
| 2019/0078239 A1 | 3/2019 | Ando et al. |
| 2019/0267538 A1* | 8/2019 | Yoshida ................. H10N 30/60 |
| 2019/0281820 A1 | 9/2019 | Usui et al. |

FOREIGN PATENT DOCUMENTS

| | | |
|---|---|---|
| JP | 2018090950 A | 6/2018 |
| JP | 2019179877 A | 10/2019 |
| WO | 2018084054 A1 | 5/2018 |

OTHER PUBLICATIONS

Takaki, Koichi; "Agricultural and Food Processing Applications of High-Voltage and Plasma Technologies"; J. HTSJ, vol. 51, No. 216, Jul. 2012, pp. 64-69. (Translation of Section 5 p. 67 "Freshness retention and component extraction by high voltage").

Microorganism Control—Science and Engineering published by Kodansha Ltd, Copyright T. Tsuchido, H. Kourai, H. Matsuoka, J. Koizumi, 2002; "Electrical Control" Section 4.1.3, p. 50 (Translation of section 4.1.3, p. 50).

* cited by examiner

CYLINDRICAL STRUCTURE

CROSS REFERENCE TO RELATED APPLICATIONS

The present application is a continuation of International application No. PCT/JP2020/043597, filed Nov. 24, 2020, which claims priority to Japanese Patent Application No. 2019-212117, filed Nov. 25, 2019, the entire contents of each of which are incorporated herein by reference.

FIELD OF THE INVENTION

The present invention relates to a cylindrical structure that generates an electric field.

BACKGROUND OF THE INVENTION

Patent Document 1 discloses a thread that generates an electric field. The thread disclosed in Patent Document 1 includes charge-generating fibers that generate an electric charge from the input of external energy. The thread disclosed in Patent Document 1 exerts an antibacterial effect by an electric field or an electric current generated between the threads.

Patent Document 1: Japanese Patent Application Laid-Open No. 2018-090950

SUMMARY OF THE INVENTION

The thread disclosed in Patent Document 1 locally generates an electric field in a micro space between the threads. Therefore, the area where the antibacterial effect can be obtained by the electric field is narrow.

An object of the present invention is to provide a cylindrical structure that exhibits an antibacterial effect in a wide area.

The cylindrical structure of the present invention includes a first cloth including a piezoelectric thread that generates an electric potential from external energy, a second cloth including a piezoelectric thread that generates an electric potential from external energy, and a connection portion connecting the first cloth and the second cloth, wherein the first cloth and the second cloth forms a side face of the cylindrical structure.

When the cylindrical structure according to the present invention is given energy from the outside, the first cloth generates a positive charge and the second cloth generates a negative charge. Because the first cloth and the second cloth are arranged on the side face of the cylindrical structure, they face each other. As a result, an electric field is generated between the first cloth and the second cloth. Therefore, the cylindrical structure can exert an antibacterial effect in a wide area between the first cloth and the second cloth.

According to the present invention, the antibacterial effect can be exhibited in a wide area.

DETAILED DESCRIPTION OF THE INVENTION

Figure 1A:
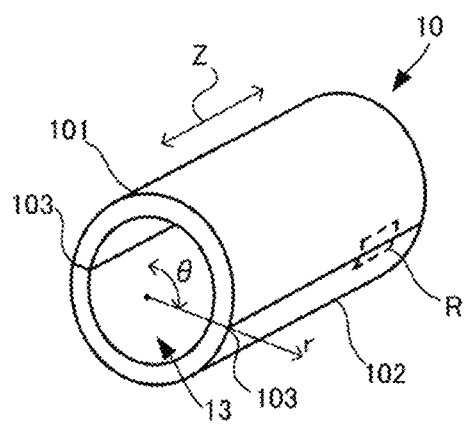
FIG. 1(A) is a perspective view showing a configuration of a cylindrical structure according to a first embodiment.
Figure 1B:
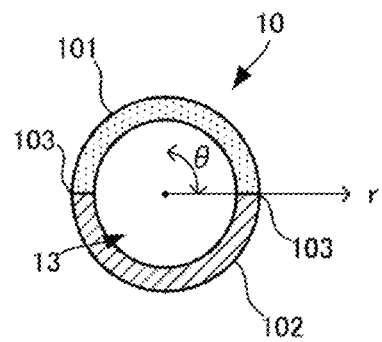
FIG. 1(B) is sectional view of the cylindrical structure cut perpendicularly to the axial direction of FIG. 1(A)
Figure 1C:
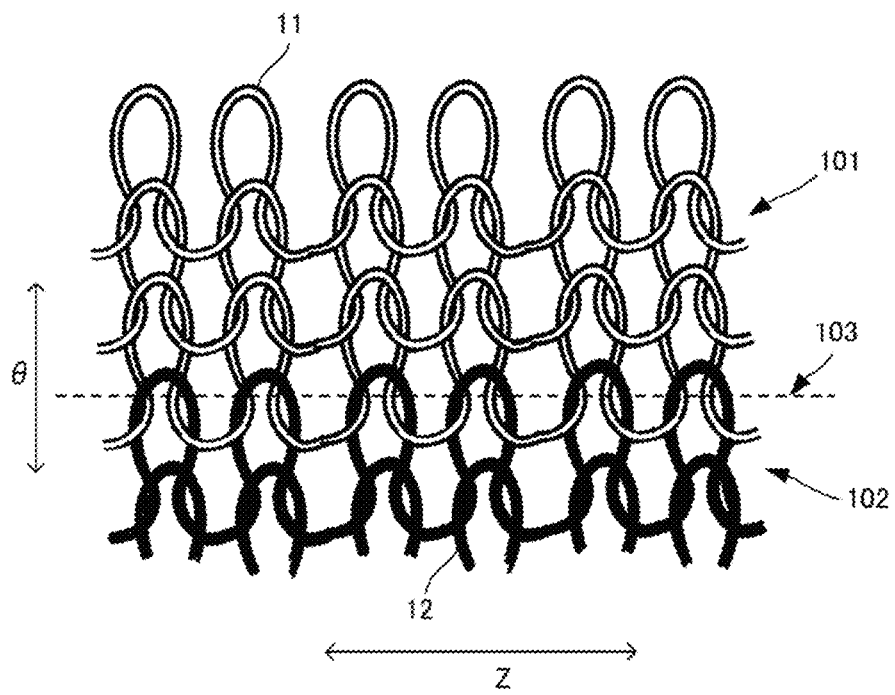
FIG. 1(C) is a partial enlarged view of a first cloth and a second cloth according to the first embodiment.

FIG. 1(A) is a perspective view showing a configuration of a cylindrical structure 10 according to a first embodiment, FIG. 1(B) is a sectional view of the cylindrical structure 10 cut perpendicularly to the axial direction, and FIG. 1(C) is a partial enlarged view of a first cloth 101 and a second cloth 102 according to the first embodiment. FIG. 1(C) is an enlarged view of the area R shown in FIG. 1(A). Hereinafter, description is made in which the axial direction of the cylindrical structure 10 is a Z direction, the radial direction is an r direction, and the circumferential direction is a θ direction.

As shown in FIGS. 1(A) and 1(B), the cylindrical structure 10 is a cylindrical structure having a hollow 13 inside. The cylindrical structure 10 includes a first cloth 101 and a second cloth 102. The first cloth 101 and the second cloth 102 form a side face of the cylindrical structure 10. The first cloth 101 is connected to the second cloth 102 at an end portion 103 in the θ direction of the cylindrical structure 10. As a result, in the cylindrical structure 10, the first cloth 101 faces the second cloth 102 with the hollow 13 interposed therebetween.

As shown in FIG. 1(C), the first cloth 101 includes a first piezoelectric thread 11. The first cloth 101 is a flat knitted fabric in which the first piezoelectric thread 11 is knitted. The first cloth 101 has a structure in which loops made of the first piezoelectric thread 11 are hooked in order along the θ direction. The second cloth 102 includes a second piezoelectric thread 12. The second cloth 102 is a flat knitted fabric in which the second piezoelectric thread 12 is knitted, similarly to the first cloth 101. At the end portion 103, the first piezoelectric thread 11 and the second piezoelectric thread 12 are knitted together. The first cloth 101 may be stitched and connected to the second cloth 102 at the end portion 103, or may be connected by an adhesive or a pressure-sensitive adhesive. In the description of the area R, the area R is assumed to be a plane face. The area R is curved along the θ direction in practice. The first cloth 101 may be formed from a plurality of first piezoelectric threads 11, and the second cloth 102 may be formed from a plurality of second piezoelectric threads 12. Both the first cloth 101 and the second cloth 102 may be formed from the first piezoelectric thread 11, and both the first cloth 101 and the second cloth 102 may be formed from the second piezoelectric thread 12.

In the present specification, "cylindrical" means a so-called tubular shape, and the shape includes for example a shape in which a part of the side face is flat, a shape in which the whole side face is flat, and a solid shape without the hollow 13. Because the first cloth 101 and the second cloth 102 are made of knitted fabrics, they are highly stretchable and easily deformed as compared with the case of being made of woven fabrics. Therefore, the cylindrical structure 10 easily curves as a whole as compared with the case of being made of a woven fabric. However, the cylindrical structure 10 of the present invention may be made of a woven fabric.

Further, a structure having a section like a corrugated board structure is also a continuum of a cylindrical structure, and is included in "cylindrical structure" of the present specification. The cylindrical structure 10 also includes, for example, a sectional shape formed from a double raschel (warp knitting), a double weave, or the like.

The plurality of first piezoelectric threads 11 are restrained from each other by being entangled with each other. When the first cloth 101 is stretched in the Z direction or the θ direction, the plurality of first piezoelectric threads 11 are pulled in the Z direction or the θ direction. When the plurality of first piezoelectric threads 11 are pulled with a force of a certain degree or more, the flexure of the loops disappears. At this time, because the plurality of first piezoelectric threads 11 are restrained from each other, each of the first piezoelectric threads 11 itself is stretched in its axial direction. Similarly, the plurality of second piezoelectric threads 12 are restrained from each other by being entangled with each other. Therefore, when the second cloth 102 is stretched in the Z direction or the θ direction with a force of a certain degree or more, each of the second piezoelectric threads 12 itself is stretched in its axial direction.

The first piezoelectric thread 11 generates a negative charge on the surface from external energy, for example, stretching. The second piezoelectric thread 12 generates a positive charge on the surface from external energy, for example, stretching.

Figure 2A:
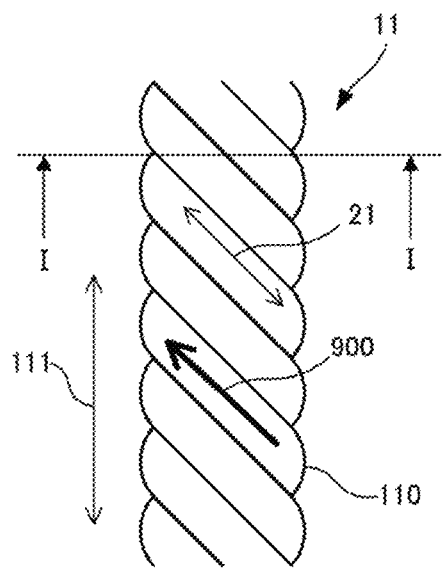
FIG. 2(A) is a partial enlarged view for explaining a configuration of a first piezoelectric thread according to the first embodiment.
Figure 2B:
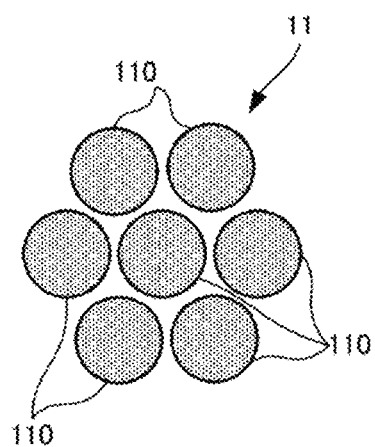
FIG. 2(B) is a sectional view taken along line I-I in FIG. 2(A).

FIG. 2(A) is a partial enlarged view for explaining a configuration of the first piezoelectric thread 11 according to the first embodiment, and FIG. 2(B) is a sectional view taken along line I-I in FIG. 2(A). Hereinafter, the first piezoelectric thread 11 will be described, and for the second piezoelectric thread 12, only differences from the first piezoelectric thread 11 will be described.

As shown in FIG. 2(A) and FIG. 2(B), the first piezoelectric thread 11 is a twisted thread (multifilament thread) formed by twisting a plurality of piezoelectric fibers 110. In FIG. 2(A) and FIG. 2(B), the first piezoelectric thread 11 in which seven piezoelectric fibers 110 are twisted is shown as one example, but the number of the piezoelectric fibers 110 is not limited to this, and the number is set appropriately in consideration of the usage and the like in practice.

The piezoelectric fiber 110 is one example of a charge-generating fiber that generates an electric charge from external energy. The piezoelectric fiber 110 is made of a functional polymer, for example, a piezoelectric polymer. Examples of the piezoelectric polymer include PVDF and polylactic acid (PLA). Polylactic acid (PLA) is a piezoelectric polymer that does not have pyroelectricity. Polylactic acid becomes piezoelectric by being uniaxially drawn. Polylactic acid includes PLLA in which an L-form monomer is polymerized and PDLA in which a D-form monomer is polymerized. The piezoelectric fiber 110 may further contain a component other than the functional polymer as long as it does not inhibit the function of the functional polymer.

Polylactic acid is a chiral polymer, whose main chain has a spiral structure. Polylactic acid exhibits piezoelectricity when it is uniaxially drawn and the molecules are oriented. When a heat treatment is further applied to increase the crystallinity, the piezoelectric constant increases. The piezoelectric fiber 110 made of uniaxially drawn polylactic acid has tensor components of $d_{14}$ and $d_{25}$ as piezoelectric strain constants where the thickness direction is defined as a first axis, a drawing direction 900 is defined as a third axis, and the direction orthogonal to both the first axis and the third axis is defined as a second axis. Therefore, polylactic acid most efficiently generates an electric charge when strain occurs in the direction of 45 degrees with respect to the uniaxially drawn direction.

Figure 3A:
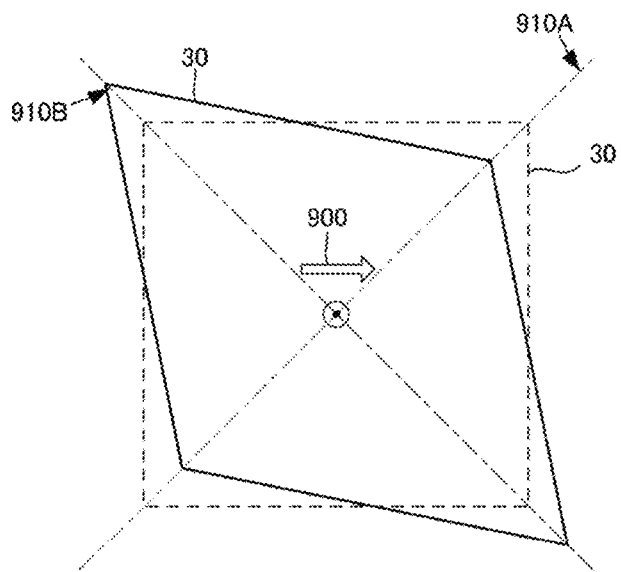
FIGS. 3(A) and 3(B) are views showing the relationship between a uniaxial drawing direction of a polylactic acid film, an electric field direction, and a deformation of the polylactic acid film.
Figure 3B:
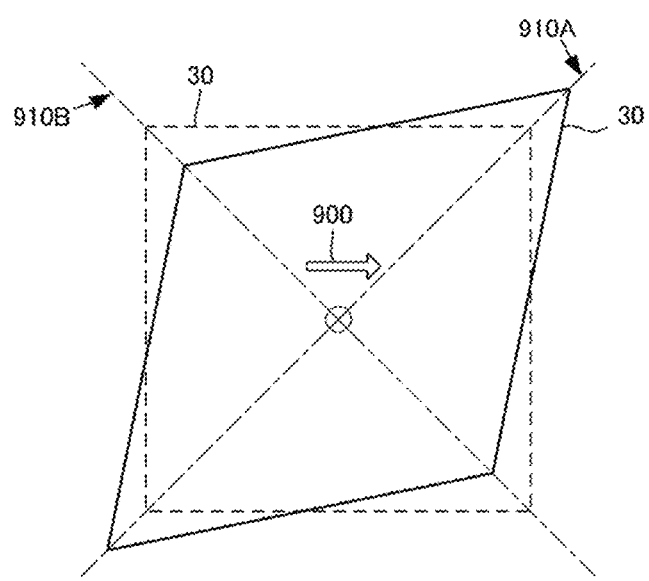

FIG. 3(A) and FIG. 3(B) are views showing the relationship between a uniaxial drawing direction of a polylactic acid film 30, an electric field direction, and a deformation of the polylactic acid film 30. The polylactic acid film 30 of FIG. 3(A) and FIG. 3(B) is a model case in which the piezoelectric fiber 110 is assumed to have a film shape. As shown in FIG. 3(A), when the polylactic acid film 30 shrinks in the direction of a first diagonal line 910A and stretches in the direction of a second diagonal line 910B orthogonal to the first diagonal line 910A, it generates an electric field in the direction from the back side to the front side of the plane of paper. That is, the polylactic acid film 30 generates a negative charge on the front side of the paper. As shown in FIG. 3(B), the polylactic acid film 30 also generates an electric charge when it stretches in the direction of the first diagonal line 910A and shrinks in the direction of the second diagonal line 910B, but the polarity is reversed and an electric field is generated in the direction from the front side to the back side of the plane of paper. That is, the polylactic acid film 30 generates a positive charge on the front side of the paper.

Because polylactic acid obtains piezoelectricity by the molecular orientation treatment by drawing, there is no need of a polling treatment unlike other piezoelectric polymers such as PVDF or piezoelectric ceramics. The uniaxially drawn polylactic acid has a piezoelectric constant of about 5 to 30 pC/N, which is a very high piezoelectric constant among polymers. Furthermore, the piezoelectric constant of polylactic acid does not fluctuate with time and is extremely stable.

The piezoelectric fiber 110 is a fiber having a circular section. The piezoelectric fiber 110 is produced by, for example, a method of extrusion-molding a piezoelectric polymer into fibers, a method of melt-spinning a piezoelectric polymer into fibers (for example, a spinning/drawing method in which a spinning step and a drawing step are performed separately, a straight drawing method in which a spinning step and a drawing step are connected, a POY-DTY method in which a drew texturizing step can also be performed at the same time, an ultra-high speed spinning method that aims speeding up, or the like), a method of fiberizing a piezoelectric polymer by dry or wet spinning (for example, a phase separation method or a dry-wet spinning method in which a polymer as a raw material is dissolved in a solvent and extruded from a nozzle to form fibers, or a gel spinning method in which a polymer is uniformly fiberized into a gel while containing a solvent, a method of fiberizing with a liquid crystal solution or a melt, or the like), a method of fiberizing a piezoelectric polymer by electrostatic spinning, or the like. The sectional shape of the piezoelectric fiber 110 is not limited to a circular shape.

The first piezoelectric thread 11 is a right swirl thread (hereinafter referred to as S thread) twisted by swirling a plurality of PLLA piezoelectric fibers 110 to the right. The second piezoelectric thread 12 is a left swirl thread (hereinafter referred to as Z thread) twisted by swirling a plurality of PLLA piezoelectric fibers 110 to the left. The first piezoelectric thread 11 and the second piezoelectric thread 12 may be spun threads, non-twisted threads, or drew texturized threads.

The drawing direction 900 of each piezoelectric fiber 110 coincides with the axial direction 21 of each piezoelectric fiber 110. In the first piezoelectric thread 11, the drawing direction 900 of each piezoelectric fiber 110 is in a state of being tilted 45 degrees to the left with respect to an axial direction 111 of the first piezoelectric thread 11. In the second piezoelectric thread 12, the drawing direction 900 of each piezoelectric fiber 110 is in a state of being tilted 45 degrees to the right with respect to the axial direction of the second piezoelectric thread 12. The angle of tilt of the drawing direction 900 with respect to the axial direction 111 of the first piezoelectric thread 11 depends on the number of twists of the piezoelectric fiber 110. As the number of twists of the piezoelectric fibers 110 increases, the angle of tilt of the drawing direction 900 of each piezoelectric fiber 110 with respect to the axial direction 111 of the first piezoelectric thread 11 increases. Therefore, in the first piezoelectric thread 11 or the second piezoelectric thread 12, the angle of tilt of the piezoelectric fiber 110 with respect to the axial direction 111 of the first piezoelectric thread 11 or the second piezoelectric thread 12 can be adjusted by adjusting the number of twists of the piezoelectric fiber 110.

Figure 4A:
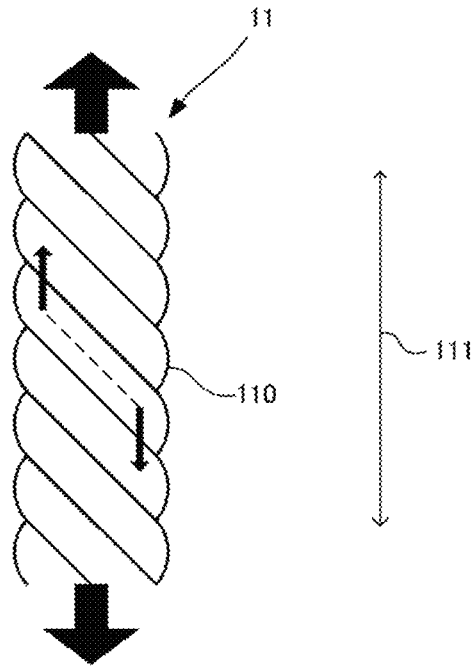
FIG. 4(A) is a view showing shear stress generated in each piezoelectric fiber when a tension is applied to the first piezoelectric thread.
Figure 4B:
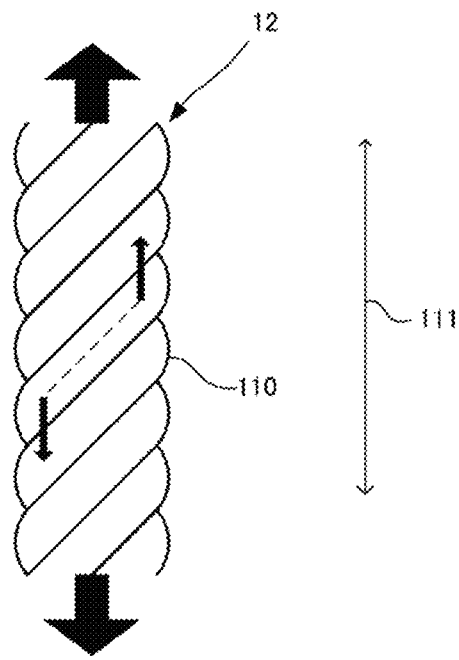
FIG. 4(B) is a view showing shear stress generated in each piezoelectric fiber when a tension is applied to a second piezoelectric thread.

FIG. 4(A) shows shear stress generated in each piezoelectric fiber 110 when a tension is applied to the first piezoelectric thread 11, and FIG. 4(B) shows shear stress generated in each piezoelectric fiber 110 when a tension is applied to the second piezoelectric thread 12.

As shown in FIG. 4(A), when an external force (tension) in the axial direction 111 is applied to the first piezoelectric thread 11, the piezoelectric fiber 110 reaches a state as shown in FIG. 3(A) and generates a negative charge on the surface. The first piezoelectric thread 11 generates a negative charge on the surface when an external force is applied. As shown in FIG. 4(B), when an external force (tension) is applied to the second piezoelectric thread 12, the piezoelectric fiber 110 reaches a state as shown in FIG. 3(B) and generates a positive charge on the surface. The second piezoelectric thread 12 generates a positive charge on the surface when an external force is applied.

Figure 5:
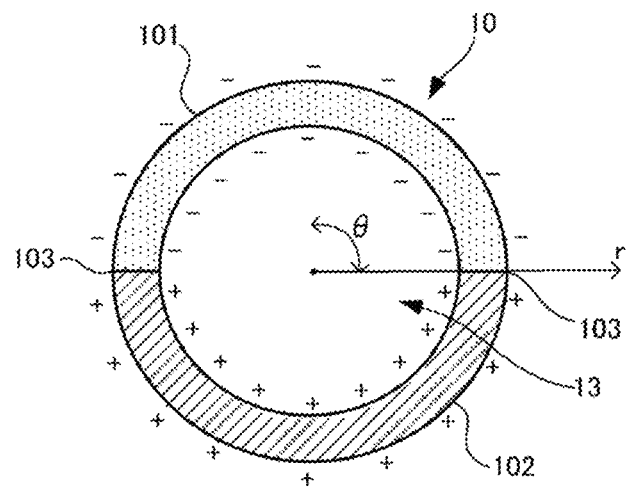
FIG. 5 is a sectional view schematically showing a part of a cylindrical structure for explaining an electric charge generated in the cylindrical structure.

FIG. 5 is a sectional view schematically showing a part of the cylindrical structure 10 cut perpendicularly to the Z direction for explaining an electric charge generated in the cylindrical structure 10. The cylindrical structure 10 includes the first cloth 101 including a plurality of first piezoelectric threads 11 and the second cloth 102 having a plurality of second piezoelectric threads 12. When the cylindrical structure 10 stretches in the 8 direction or the Z direction, the first cloth 101 and the second cloth 102 stretch. The plurality of first piezoelectric threads 11 and the plurality of second piezoelectric threads 12 stretch in their respective axial directions. The plurality of first piezoelectric threads 11 stretched in the axial direction generate a negative charge on the surface. The plurality of second piezoelectric threads 12 stretched in the axial direction generate a positive charge on the surface. Therefore, when the cylindrical structure 10 stretches, it generates a negative charge on the surface of the first cloth 101 and a positive charge on the surface of the second cloth 102, as shown in FIG. 5.

The end portion 103 where the first cloth 101 and the second cloth 102 contact each other has the same potential. At this time, the portion other than the end portion 103 of the first cloth 101 has a lower negative potential in order to maintain the original potential difference from the second cloth 102 as a whole of the first cloth 101. The portion of the second cloth 102 other than the end portion 103 has a higher positive potential in order to maintain the original potential difference from the first cloth 101 as a whole of the second cloth 102. Therefore, the first cloth 101 and the second cloth 102 generate an electric field at a portion where they face each other except the end portion 103. That is, a strong electric field is formed in the hollow 13 which is a wide area surrounded by the first cloth 101 and the second cloth 102. Therefore, the cylindrical structure 10 can generate an electric field in a wide area.

It has been known that electric fields can suppress the growth of bacteria and fungi (see, for example, Tetsuaki Tsuchido, Hiroki Kourai, Hideaki Matsuoka, Jun-ichi Koizumi, *Microorganism Control-Science and Engineering*, Kodansha. See also, for example, Koichi Takaki, Agricultural and Food Processing Applications of High-Voltage and Plasma Technologies, J. HTSJ, Vol. 51, No. 216). In addition, due to the electric potential that causes an electric field, an electric current may flow through a current path formed by moisture or the like, or through a circuit formed by a local micro discharge phenomenon or the like. It is considered that this electric current weakens bacteria and suppresses the growth of bacteria. The bacteria referred to in this embodiment includes bacteria, fungi, and a microorganism such as mites and fleas.

Therefore, the cylindrical structure 10 directly exerts an antibacterial effect by the electric field formed in the hollow 13. That is, the cylindrical structure 10 exerts an antibacterial effect against the bacteria taken into the hollow 13. As a result, the cylindrical structure 10 can exert an antibacterial effect in a wide area between the first cloth 101 and the second cloth 102 where the faces of the first cloth 101 and the second cloth 102 face each other.

In addition, the cylindrical structure 10 exerts an antibacterial effect directly by an electric field formed in the vicinity of the cylindrical structure 10 or by an electric field generated when the cylindrical structure 10 comes close to an object having a predetermined potential such as a human body. Alternatively, the cylindrical structure 10 passes an electric current through moisture such as sweat when the cylindrical structure 10 comes close to another nearby fiber or an object having a predetermined potential such as a human body. The cylindrical structure 10 directly exerts an antibacterial effect by this electric current as well in some cases. Alternatively, the cylindrical structure 10 indirectly exerts an antibacterial effect by reactive oxygen species in which oxygen contained in water is changed by the action of electric current or voltage, radical species generated by interaction or catalysis with additives contained in fibers, or other antibacterial chemical species (amines derivatives, etc.), in some cases. Alternatively, in some cases, oxygen radicals are generated in the cells of bacteria by the stress environment due to the presence of an electric field or an electric current, and the cylindrical structure 10 indirectly exerts an antibacterial effect by the oxygen radicals in some cases. As the radical, generation of superoxide anion radical (reactive oxygen) or hydroxyl radical can be considered. "Antibacterial" as used in the present embodiment is a concept including both an effect of suppressing the growth of bacteria and an effect of killing bacteria.

As the thread that generates a negative charge on the surface, the Z thread using PDLA can be considered in addition to the S thread using PLLA. As the thread that generates a positive charge on the surface, the S thread using PDLA can be considered in addition to the Z thread using PLLA.

The first cloth 101 and the second cloth 102 may include a non-piezoelectric thread. Here, the non-piezoelectric thread includes a thread made of natural fibers or synthetic fibers typically used as a thread and which does not generate an electric charge from external energy. Examples of the natural fiber include cotton, wool, and hemp. Examples of the synthetic fiber include polyester, polyurethane, rayon, cupra, and acetate. The non-piezoelectric thread may be a twisted thread obtained by twisting natural fibers or synthetic fibers. The strength or the degree of stretch of the first cloth 101 and the second cloth 102 can be adjusted by selecting the material of the non-piezoelectric thread or the amount of the non-piezoelectric thread to be included.

The first cloth 101 may have a structure in which the loops of the first piezoelectric thread 11 are hooked in order along the Z direction. Similarly, the second cloth 102 may have a structure in which loops of the second piezoelectric thread 12 are hooked in order along the Z direction.

The first cloth 101 or the second cloth 102 may be a woven fabric. In this case, the first piezoelectric thread 11 is included in the warp or weft of the first cloth 101. The second piezoelectric thread 12 is included in the warp or weft of the second cloth 102. When the cylindrical structure 10 is stretched, the first piezoelectric thread 11 or the second piezoelectric thread 12 is pulled in the axial direction of each piezoelectric thread. As a result, the cylindrical structure 10 can exert an antibacterial effect. Further, the first cloth 101 or the second cloth 102 may be a non-woven fabric.

Figure 6A:
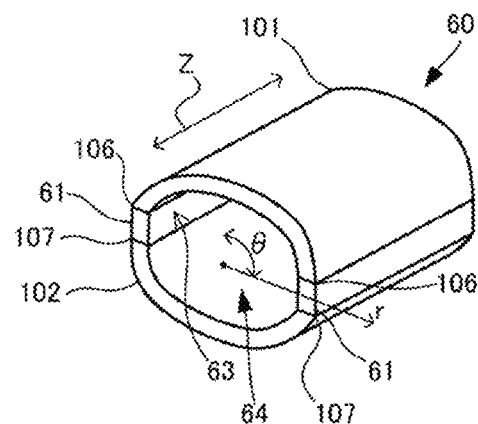
FIG. 6(A) is a perspective view showing a configuration of a cylindrical structure according to a second embodiment.
Figure 6B:
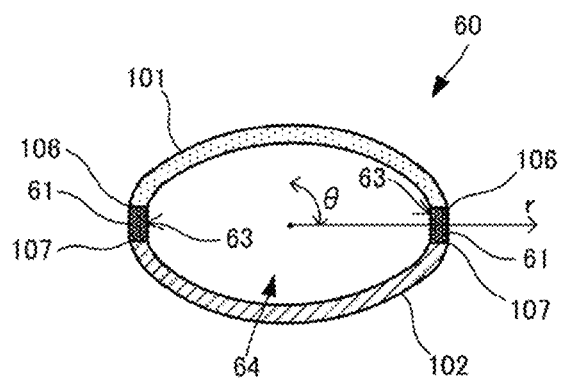
FIG. 6(B) is a sectional view of the cylindrical structure cut perpendicularly to the axial direction of FIG. 6(A).

Hereinafter, a cylindrical structure 60 according to a second embodiment will be described. FIG. 6(A) is a perspective view showing a configuration of the cylindrical structure 60 according to the second embodiment, and FIG. 6(B) is a sectional view of the cylindrical structure 60 cut perpendicularly to the axial direction. In the description of the cylindrical structure 60, only the points different from those of the first embodiment will be described, and the same points will be omitted.

As shown in FIG. 6(A) and FIG. 6(B), the cylindrical structure 60 includes a joint portion 61. The joint portion 61 is located between the first cloth 101 and the second cloth 102. The joint portion 61 connects an end portion 106 of the cylindrical structure 60 in the first cloth 101 in the 8 direction and an end portion 107 of the cylindrical structure 60 in the second cloth 102 in the 8 direction.

The joint portion 61 includes an inner face 63 that is inside the cylindrical structure 60. The joint portion 61 joins the first cloth 101 and the second cloth 102 such that a hollow 64 is formed between the first cloth 101 and the second cloth 102. The cylindrical structure 60 generates an electric field between the first cloth 101 and the second cloth 102. As a result, the cylindrical structure 60 can exert an antibacterial effect by the electric field generated in the hollow 64.

When the joint portion 61 is made of a material that does not get electrified, the cylindrical structure 60 also generates an electric field at the joint portion 61. That is, the cylindrical structure 60 also generates an electric field between the end portion 106 of the first cloth 101 and the end portion 107 of the second cloth 102. Therefore, the cylindrical structure 60 can generate an electric field in a wider range than in the case where the joint portion 61 is not provided. As a result, the cylindrical structure 60 can exert an antibacterial effect in a wide range.

The joint portion 61 is preferably made of a material having a higher friction coefficient than the first cloth 101 and the second cloth 102. When a user wears the cylindrical structure 60 on the body, for example, when the cylindrical structure 60 is attached to the arm, the inside of the cylindrical structure 60 comes into contact with the user's body. At this time, when the friction coefficient of the joint portion 61 is high, the inner face 63 of the joint portion 61 can exert an anti-slip effect on the user's body or the like.

When the cylindrical structure 60 receives a deforming force from the outside, the joint portion 61 is less likely to be deformed than the first cloth 101 and the second cloth 102 because it is difficult to slip on the user's body or the like. That is, when the cylindrical structure 60 receives a deforming force from the outside, the first cloth 101 and the second cloth 102 are more likely to be deformed than the joint portion 61. As a result, the cylindrical structure 60 can deform the first cloth 101 and the second cloth 102 with a small force. Therefore, the first cloth 101 and the second cloth 102 can generate an electric field with a small force.

The stretchability of the joint portion 61 and the first cloth 101 and the second cloth 102 may be similar, but when the joint portion 61 is less stretchable than the first cloth 101 and the second cloth 102, it is preferable that the joint portion 61 is formed from a woven fabric, and the first cloth 101 and the second cloth 102 are formed from knitted fabrics. For example, woven fabrics are usually less stretchable than knitted fabrics. When the joint portion 61, the first cloth 101, and the second cloth 102 are formed from knitted fabrics, the stretchability may be changed by changing the knitting structure. The joint portion 61, which is difficult to stretch, restrains the end portion 106 of the first cloth 101 and the end portion 107 of the second cloth 102. Therefore, when the cylindrical structure 60 receives a deforming force from the outside, the first cloth 101 and the second cloth 102 are greatly distorted as compared with the case of knitted fabric alone. As a result, the cylindrical structure 60 can efficiently generate an electric field when it receives a small force.

The joint portion 61 is preferably made of a material having a higher hydrophilicity than the first cloth 101 and the second cloth 102, for example, ordinary thread. That is, the joint portion 61 is made of a material having a higher hydrophilicity than the first cloth 101 and the second cloth 102 containing PLLA. Because the joint portion 61 has a higher hydrophilicity than the first cloth 101 and the second cloth 102, moisture easily permeates into the inside of the joint portion 61. Therefore, the joint portion 61 easily absorbs moisture or fine particles. Therefore, the cylindrical structure 60 can easily take in moisture or fine particles into the joint portion 61 from the outside. In addition, the cylindrical structure 60 can easily take in moisture or fine particles from the outside into the hollow 64 through the joint portion 61. Because of this, the cylindrical structure 60 can exert an antibacterial effect more efficiently than when a material having a low hydrophilicity is used for the joint portion 61.

When the hydrophilicity of the joint portion 61 is high, moisture quickly wets and spreads inside the joint portion 61. Moisture that has spread over a wide area inside the joint portion 61 has a large surface area and is easily vaporized. Usually, hydrophilic fiber aggregates have high drying properties. Because moisture evaporates quickly inside the joint portion 61, the cylindrical structure 60 can quickly exert an antibacterial effect.

Figure 7A:
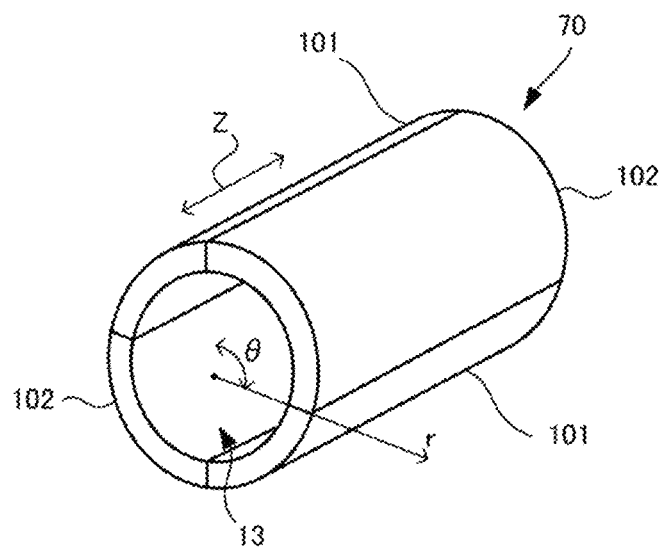
FIG. 7(A) is a perspective view showing a configuration of a cylindrical structure according to a third embodiment.
Figure 7B:
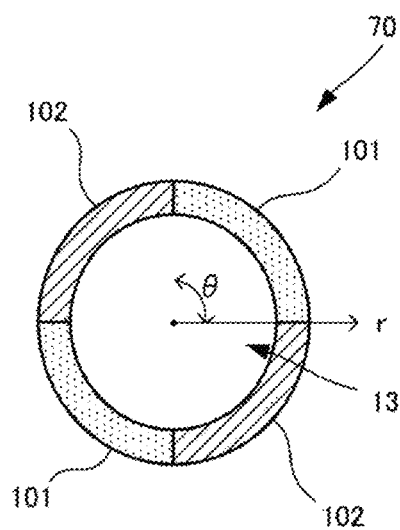
FIG. 7(B) is sectional view of the cylindrical structure cut perpendicularly to the axial direction of FIG. 7(A).

Hereinafter, a cylindrical structure 70 according to a third embodiment will be described. FIG. 7(A) is a perspective view showing a configuration of the cylindrical structure 70 according to the third embodiment, and FIG. 7(B) is a sectional view of the cylindrical structure 70 cut perpendicularly to the axial direction. In the description of the cylindrical structure 70, only the points different from the cylindrical structure 10 of the first embodiment will be described, and the same points will be omitted.

As shown in FIG. 7(A) and FIG. 7(B), the cylindrical structure 70 has a plurality of first cloths 101 and second cloths 102. The first cloths 101 face each other and the second cloths 102 face each other. Therefore, the cylindrical structure 70 can exert an antibacterial effect by an electric field generated between the first cloths 101 and the second cloths 102.

Figure 8A:
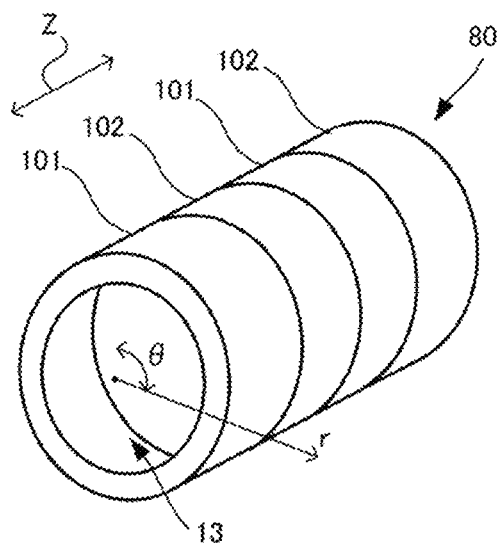
FIG. 8(A) is a perspective view showing a configuration of a cylindrical structure according to a fourth embodiment.
Figure 8B:
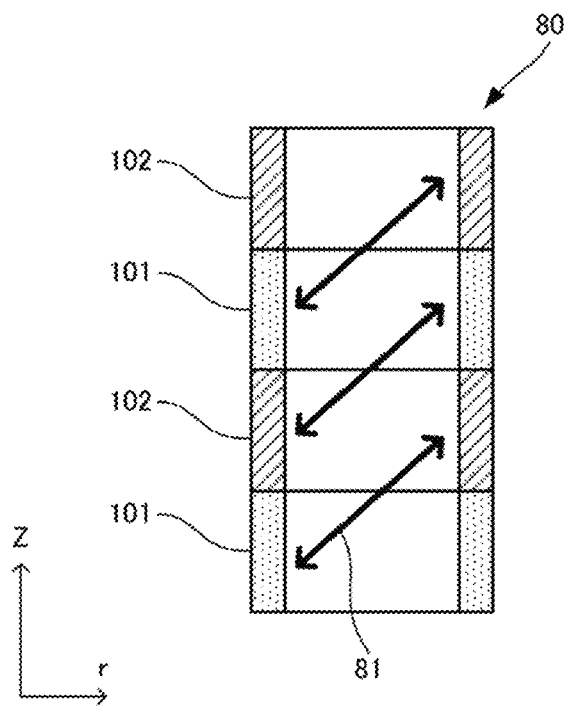
FIG. 8(B) is a sectional view of the cylindrical structure cut in the axial direction of FIG. 8(A).

FIG. 8(A) is a perspective view showing a configuration of a cylindrical structure 80 according to a fourth embodiment, and FIG. 8(B) is a sectional view of the cylindrical structure 80 cut in the axial direction. In the description of the cylindrical structure 80, only the points different from the cylindrical structure 10 of the first embodiment will be described, and the same points will be omitted.

As shown in FIG. 8(A) and FIG. 8(B), the cylindrical structure 80 has a plurality of first cloths 101 and second cloths 102. Each first cloths 101 and each second cloths 102 are arranged alternately along the Z direction. The first cloths 101 and the second cloths 102 are slanted as shown by arrows 81 shown in FIG. 8(B). In this case as well, the cylindrical structure 80 forms an electric field between the first cloths 101 and the second cloths 102. Therefore, the cylindrical structure 80 can exert an antibacterial effect by the electric field generated between the first cloths 101 and the second cloths 102.

The cylindrical structure 10, the cylindrical structure 60, the cylindrical structure 70, or the cylindrical structure 80 described above can be applied to various clothing or products such as medical components. For example, the cylindrical structure 10, the cylindrical structure 60, the cylindrical structure 70, or the cylindrical structure 80 may be applied to masks, gloves, clothing, underwear (especially socks and belly bands), towels, headbands, wristbands, general sportswear, hats, bedclothes (including duvets, mattresses, sheets, pillows, and pillowcases), filters for water purifiers, air conditioners, and air purifiers, pet-related products (pet mats, pet clothes, pet inner clothes), various mats (for feet, hands, toilet seats, etc.), bags such as tote bags, laundry nets, packaging materials such as tangerine nets, seats (seats for cars, trains, planes, etc.), sofa covers, bandages, gauze, sutures, clothes for doctors and patients, supporters, sanitary goods, sports goods (clothes, inner gloves, gauntlets used in martial arts, etc.), artificial blood vessels, medical components for operations, and the like.

Finally, the description of this embodiment should be considered to be exemplary in all respects and not restrictive. The scope of the invention is indicated by the claims, not by the embodiments described above. Furthermore, the scope of the present invention is intended to include all modifications within the meaning and scope of the claims.

DESCRIPTION OF REFERENCE SYMBOLS 10, 60, 70, 80: Cylindrical structure
11: First piezoelectric thread
12: Second piezoelectric thread
61: Joint portion
101: First cloth
102: Second cloth

The invention claimed is:

1. A cylindrical structure comprising:
a first cloth that includes a first piezoelectric thread that generates a first electric potential from input of external energy;
a second cloth that includes a second piezoelectric thread that generates a second electric potential from the input of the external energy; and
a connection portion connecting the first cloth and the second cloth,
wherein the first cloth and the second cloth form a side face of the cylindrical structure, and
wherein the first piezoelectric thread and the second piezoelectric thread generate opposite charges.

2. The cylindrical structure according to claim 1, wherein the connection portion is a joint portion between the first cloth and the second cloth and connects the first cloth and the second cloth.

3. The cylindrical structure according to claim 2, wherein the joint portion connects the first cloth and the second cloth such that a hollow is formed between the first cloth and the second cloth.

4. The cylindrical structure according to claim 2, wherein the joint portion has a higher friction coefficient than the first cloth and the second cloth.

5. The cylindrical structure according to claim 2, wherein the joint portion has a higher hydrophilicity than the first cloth and the second cloth.

6. The cylindrical structure according to claim 2, wherein the joint portion has a lower stretchability than the first cloth and the second cloth.

7. The cylindrical structure according to claim 2, wherein the first cloth and the second cloth are knitted fabrics.

8. The cylindrical structure according to claim 7, wherein the joint portion is a woven fabric.

9. The cylindrical structure according to claim 1, wherein the first cloth and the second cloth further include an ordinary thread that does not generate an electric potential from the input of the external energy.

10. The cylindrical structure according to claim 1, wherein at least one of the first piezoelectric thread and the second piezoelectric thread contains a chiral polymer.

11. The cylindrical structure according to claim 1, wherein the connection portion connects the first cloth and the second cloth such that a hollow is formed between the first cloth and the second cloth.

12. The cylindrical structure according to claim 11, wherein the cylindrical structure includes a plurality of first cloths and a plurality of second cloths, wherein the first cloths and the second cloths are arranged alternately along an axial direction of the cylindrical structure.

13. A cylindrical structure comprising:
a first cloth that includes a first piezoelectric thread that generates a first electric potential from input of external energy;
a second cloth that includes a second piezoelectric thread that generates a second electric potential from the input of the external energy; and a connection portion connecting the first cloth and the second cloth,
wherein the first cloth and the second cloth form a side face of the cylindrical structure,
wherein the connection portion connects the first cloth and the second cloth such that a hollow is formed between the first cloth and the second cloth, and
wherein the cylindrical structure includes a plurality of first cloths that face each other across the hollow, and a plurality of second cloths that face each other across the hollow.

\* \* \* \* \*